United States Patent [19]

Hudson et al.

[11] Patent Number: 4,474,947

[45] Date of Patent: Oct. 2, 1984

[54] BENZAZOLIDES AND THEIR EMPLOYMENT IN PHOSPHATE ESTER OLIGONUCLEOTIDE SYNTHESIS PROCESSES

[75] Inventors: Derek Hudson; Ronald M. Cook, both of San Rafael, Calif.

[73] Assignee: Biosearch, San Rafael, Calif.

[21] Appl. No.: 366,537

[22] Filed: Apr. 8, 1982

[51] Int. Cl.$^3$ .............................................. C07H 19/10
[52] U.S. Cl. ....................................... 536/27; 536/28; 536/29; 548/111; 548/259
[58] Field of Search .............................. 536/27, 28, 29

[56] References Cited

U.S. PATENT DOCUMENTS

| | | | |
|---|---|---|---|
| 3,986,967 | 10/1976 | Okorodu | 548/111 |
| 4,174,285 | 11/1979 | Braid | 548/259 |
| 4,310,662 | 1/1982 | Crea | 536/29 |

FOREIGN PATENT DOCUMENTS 2007670  5/1979  United Kingdom .

OTHER PUBLICATIONS

Cole, B. H., "Making Genes with Machines", *High Technology*, vol. 1, No. 1, 60–68.
Itakura, et al., "A Modified Triester Method for the Synthesis of Deoxyribopolynucleotides", *Car J. Chem.*, 41,3649 (1973).
Broka, C., et al., "Simplifications in the Synthesis of Oligonucleotide Blocks", *Nucleic Acid Res.* 8,5461, 1980.
Amarnath V. et al., "Chemical Synthesis of Oligonucleotides" *Chem. Rev.* 1977, 77, 183, (1977).
Itakura K. et al., "Chemical DNA Synthesis and Recombinant DNA Studies" *Science* 209, 1401 (1980).

*Primary Examiner*—Johnnie R. Brown
*Assistant Examiner*—Elli Peselev
*Attorney, Agent, or Firm*—Ciotti & Murashige

[57] ABSTRACT

Benzazoles, including benzatriazoles and benzimidazoles are employed in phospate triester oligonucleotide synthesis. The benzazoles form arylbenzazolide coupling agents, and phosphorodibenzazolides. Processes employing these reagents are also disclosed.

15 Claims, No Drawings

BENZAZOLIDES AND THEIR EMPLOYMENT IN PHOSPHATE ESTER OLIGONUCLEOTIDE SYNTHESIS PROCESSES

TECHNICAL FIELD

This invention is in the field of oligonucleotide synthesis. More particularly, it concerns a group of benzazoles and corresponding benzazolides and their use in phosphate triester oligonucleotide synthesis schemes.

THE PRIOR ART

An article "Making Genes With Machines" by B. H. Cole, appearing in *High Technology*, Vol 1, No 1, pages 60–68 provides a general overview of three fundamental processes presently of interest in the fabrication of oligonucleotides in precisely defined sequences. These three processes are known as the phosphate diester process, the phosphate triester process and the phosphite triester process.

The phosphate triester process and its basic chemistry are described in, for example, Itakura, et al, "A Modified Triester Method For the Synthesis of Deoxyribopolynucleotides", *Can.J.Chem.*, 51, 3649 (1973); "Simplifications in the Synthesis of Oligonucleotide Blocks", C. Booka, T. Hozumi, R. Arantzen & K. Itakura *Nucleic Acids Res.* 8, 5461, 1980; "Chemical Synthesis of Oligonucleotides", V. Armanath & A. D. Broom, *Chem.Rev.* 1977 77 183 (1977); "Chemical DNA Synthesis and Recombinant DNA Studies", K. Itakura & A. D. Riggs, *Science* 209, 1401, 1980, which for brevity are incorporated herein by reference.

The phosphate triester synthetic scheme conventionally proceeds as follows: a nucleotide having a protected 3' phosphate diester group is coupled with a nucleoside or nucleotide having an available free 5' hydroxyl group in the presence of a coupling agent. This procedure may be shown as

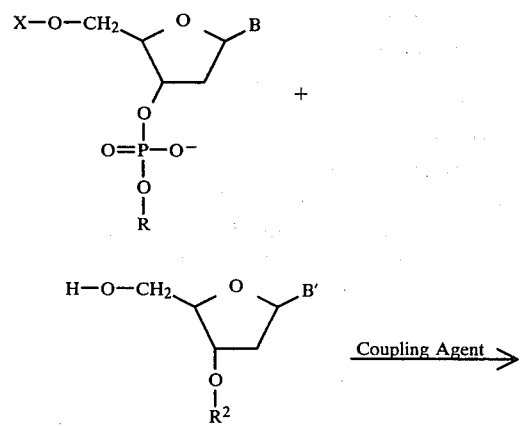

-continued

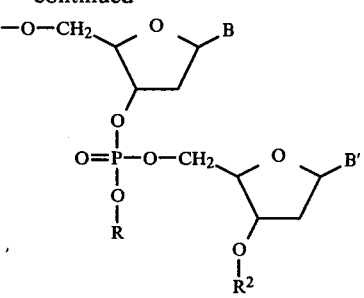

wherein X is a protecting group such as trityl, B and B' are bases (protected when required), R is a base-labile phosphate-protecting group such as p-chlorophenyl, and $R^2$ is a protecting group or a solid support upon which the lower nucleotide is temporarily affixed. Suitable coupling agents are known to include 2,4,6-triisopropylbenzenesulfonyl tetrazolide, para-nitrobenzenesulfonyl triazolide, benzenesulfonyl triazolide, benzenesulfonyl 4-nitroimidazolide, 2,4,6-trimethylbenzenesulfonyl tetrazolide, 2,4,6-triisopropylbenzenesulfonyl chloride and 2,4,6-trimethylbenzenesulfonyl chloride (G.B. Patent Application No. 2,007,670).

In working with this system for nucleotide oligomerization certain fundamental shortcomings related to the art-taught triazole and tetrazole coupling agents become apparent. For one, tetrazole is only marginally soluble in usual reaction solvents. This tendency of tetrazole to crystallize causes undesirable dilution and poses risks of clogging the microscale equipment usually employed. For another, simple triazoles and tetrazole can not be easily modified to enhance their solubility, reactivity and/or stability so that less than optimum life of very expensive reagents is observed and/or less than complete reaction often takes place. This latter failing is very serious in a multi-step oligonucleotide synthesis where usually acceptable conversion losses quickly multiply to give an unreasonable result. It is an object of this invention to provide an advanced and improved family of reagents for the phosphate triester oligonucleotide sysnthesis.

STATEMENT OF THE INVENTION

It has now been found that benzazoles of the formula

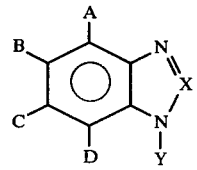

wherein X is N or CH, Y is H or an acidic leaving group and A, B, C and D are each independently selected from hydrogen and aromatic ring substituent groups, give superior results as components of coupling agents in the phosphate triester oligonucleotide synthesis scheme.

More particularly, it has been found that these benzazoles form arylsufonylbenzazolides of the formula

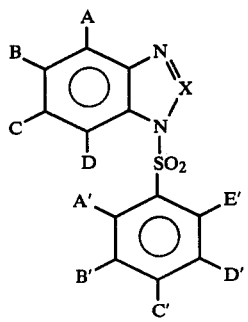

wherein X, A, B, C, and D are as previously defined and A′, B′, C′, D′ and E′ are each aromatic ring-substituenting groups or hydrogens, which are advantageous coupling agents in the phosphate triester synthesis scheme.

These benzazoles can also form phosphorodibenzazolides of the formula

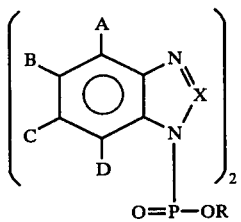

wherein R is a phosphate protecting group. These materials can be employed in phosphate ester bond-forming reactions wherein they form new benzazolide intermediates with protected nucleosides and nucleotides. These intermediates have the formula

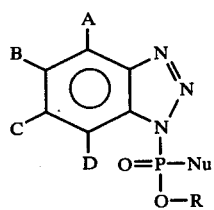

wherein A, B, C and D and X are as previously defined, R is a phosphate protecting group and Nu is a nucleoside, a nucleotide or an oligonucleotide (all with or without protecting groups).

In other aspects, this invention relates to improved phosphate triester oligonucleotide preparation processes employing these benzazoles and derivatives thereof.

DETAILED DESCRIPTION OF THE INVENTION

The Benzazoles

The benzazoles employed in this invention, while all of one family, can be broken down into benzotriazoles, i.e. materials having a structure of the formula

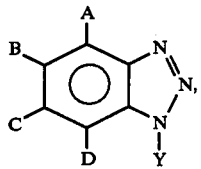

and benzimidazoles, i.e. materials having a structure of the formula

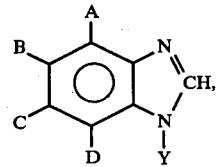

wherein Y is H or an acidic leaving group. In both cases the aromatic rings contain A, B, C and D groups on their 5, 6, 7 and 8 carbons. These may all be hydrogens or they may independently each be aromatic ring-substituenting groups known to the art of organic chemistry. The ability to make these substitutions is one of the major advantages of the present invention as it permits the solubility and reactivity/stability of the materials to be finely tuned. The substituents placed on the ring should be chemically inert under the reaction conditions encountered in oligonucleotide syntheses. Examples of suitable ring-substituenting groups include halogens, such as chloro, bromo, iodo or fluoro; lower alkyls of 1 to 4 carbons such as methyl, ethyl, propyl or the like; simple substituted alkyls such as chloromethyl, trifluoroethyl, and the like; aromatics and substituted aromatics such as benzyl, phenyl, and substituted benzyl or phenyl; lower alkoxies of 1 to 4 carbons such as methoxy, ethoxy, and n and isopropoxy; nitro, nitroso, sulfonato, amino and cyano.

As previously mentioned, the exact A, B, C and D's employed will be at least in part dictated by the properties sought. For example, when a less polar reaction medium is being employed it will often be of advantage to add relatively non-polar A, B, C and D groups, such as the lower alkyls and aromatics, to enhance solubility. Likewise, by adding electron-donating or withdrawing groups such as F, $NO_2$, $C(CH_3)_3$ $OCH_3$ (alkoxy) and the like to A, B, C or D positions, the system's reactivity/stability can be tailored.

Preferred groups, because of their ready synthesis, include those having each of A, B, C and D as hydrogens, and those having at their "5" carbon (that is, as A) Cl, Br, $NO_2$, $CH_3$, or $O-CH_3$. Other A, B, C and D substituents may be employed, as well, if desired.

The Phosphate Triester Coupling Agents

This embodiment of the invention provides arylsulfonylbenzazolides. These materials include arylsulfonylbenzotriazolides of the formula

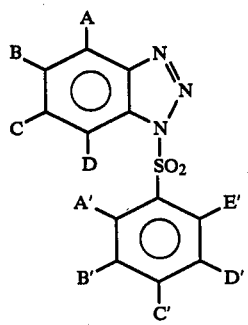

and arylsulfonyl benzimidazolides of the formula

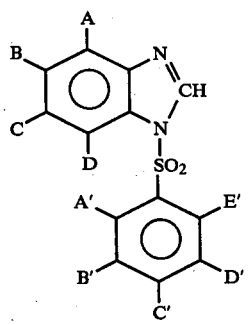

In both cases A, B, C and D are as previously described and A', B', C', D' and E' are each independently selected from hydrogen and aromatic ring substituenting groups. Two adjacent A', B', C', etc. substituents may bridge to form a second aromatic ring—i.e. to give a naphthalene structure. Usually, at least a portion of A', B', C', D' and E' are hydrogens with lower alkyls of up to 4 carbons also being preferred substituents. In general, it is preferred to have A', C' and E' as hydrogens or as the same alkyl substituent selected from among methyl, ethyl, isopropyl, n-propyl and the butyls, e.g. to give a 2,4,6-triisopropyl benzene group, a 2,4,6-trimethyl benzene group, a 2,4,6-triethyl benzene group and a benzene group.

These materials may be prepared in one step by reacting an appropriately A', B', C', D', E'-substituented arylsulfonyl halide (e.g. a benzenesulfonyl halide) with the desired benzotriazole or benzimidazole in an inert liquid phase in which both reactants dissolve. An organic base is necessary to effect elimination of the hydrogen from the triazole or imidazole and the halide from the sulfonyl halide. Examples of such bases are triethylamine, or a similar trialkylamine; pyridine or a similar aromatic amine or a similar strength insoluble basic ion exchange resin. This preparation is merely representative, other equivalent preparations may be used as well. These products may be used as especially advantageous coupling agents in the phosphate triester oligonucleotide syntheses.

The Phosphorodibenzazolides

This embodiment of the invention provides phosphorodibenzazolides of the formula

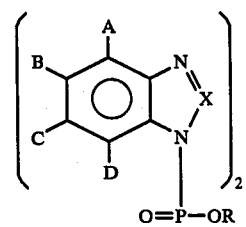

wherein X, A, B, C and D are as previously defined and R is a phosphate protecting group. These materials react with protected nucleotides and nucleosides to give new compounds of the formula

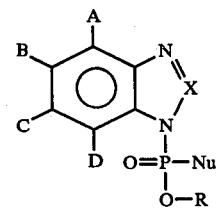

wherein A, B, C, D and X are as previously defined, R may be hydrogen but usually is a suitable base-labile phosphate protecting group. This protecting group is selected from organic groups such as a simple aliphatic or aromatic group, for example, a 1 to 4 carbon lower alkyl or a substituted or unsubstituted aromatic (6 to 12 carbon aryl, alkaryl or aralkyl) such as phenyl, 2-chlorophenyl, 2-methylphenyl, 2-bromophenyl, 4-chlorophenyl, 2,4-dichlorophenyl or the like. Other phosphate triester blocking groups taught by the art to be equivalent may be used as well. Nu is a nucleoside or nucleotide particularly one having its "5" hydroxyl and, if appropriate, its base protected. It should be noted that the symbol "Nu" and the term "nucleoside" are defined to include deoxynucleosides and likewise the term "nucleotide" includes deoxynucleotides as these are the materials usually of most interest. In addition "Nu" is defined to include oligomeric nucleotides and deoxynucleotides. These compounds can be represented in more detail by formulae I and II.

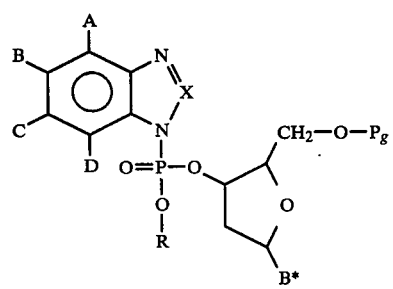

(I)

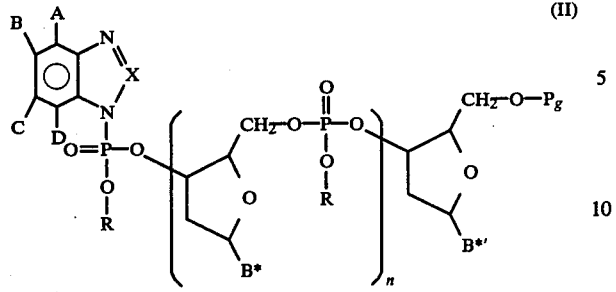

(II)

wherein A, B, C, D, X and R are as previously described. $P_g$ is a selectively removable protecting group for the nucleoside's '5 carbon hydroxyl, such as levulinyl and (most commonly) acid-labile groups like trityl (triphenylmethyl) and DMT (4,4-dimethoxytrityl). B* and B*' are each base selected from 1-thyminyl, 1-(N-protected)cytosinyl, 9-(N-protected)adeninyl or 9-(N-protected)guaninyl. The N-protecting groups are materials known in the art and typically include benzoyl groups, isobutyryl groups and anisoyl groups with the benzoyl group being the group of choice with adenine and cytosine and isobutyryl being the group of choice with guanine. n is an integer, most commonly 1 but also higher numbers such as 2, 3, 4, 5, up to 10 to 12 or more. These higher mer unit materials can be prepared with the same (or more commonly different) B* units. It should also be appreciated that nucleosides and nucleotides can simply replace the deoxy materials here shown.

These activated species may be prepared by reacting an optionally protected nucleoside or nucleotide and a phosphorodibenzazolide. This reaction is carried out in solution in a suitable organic aprotic reaction solvent such as acetonitrile, pyridine, tetrahydrofuran, dimethylformamide, 1,4-dioxan, methylene chloride, chloroform, ethyl acetate, acetone, diethyl ether, benzene and mixtures thereof. One or a minor (up to 2 fold) molar excess of the dibenzazolide is usually used. This reaction is rapid and is usually complete in 1 to 20 minutes at temperatures from −20° C. to 50° C.

This product can be further reacted with nucleotide units having free 5' hydroxyl groups to add yet further nucleotide units. Thereafter the entire oligonucleotide is recovered. The bases can be unblocked and the phosphate protecting group can be removed.

These phosphorodibenzazolides can be formed by reaction of the benzazole with a dihalogen-substituted oxyphosphorous compound such as a phosphorodichloridate, e.g. p-chlorophenylphosphorodichloridate or the like.

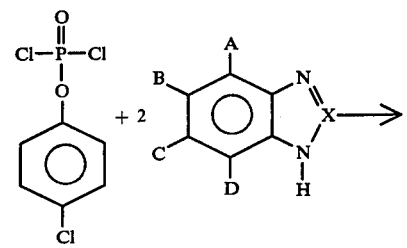

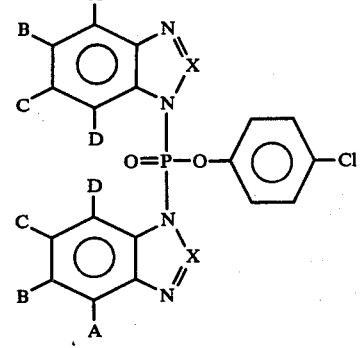

Other groups can replace the chlorophenyl group, for example lower alkyls of 1 to 4 carbons and aryls of 6 or 10 carbons all with optional substituents such as halos, alkyls, or the like. So too, other halos can replace the two chloros attached to the phosphorous.

The reaction is typically carried out for from 10 to 30 minutes at room temperature in an organic solvent such as pyridine, dioxan, tetrahydrofuran, acetonitrile, chloroform or the like. An excess of the benzazole or, optionally, a suitable organic base particularly an organic tertiary amine especially a trialkylamine having from 1 to 5 carbons per alkyl group such as trimethyl amine, diisopropylethyl amine, tributyl amine or the like, may be added to neutralize HCl generated.

The in situ-generated dibenzazolide intermediate is generally used without isolation. It is firstly reacted with a 5' protected nucleoside to give a monobenzazolide, which is further reacted with a hydroxyl component shown as HOR'.

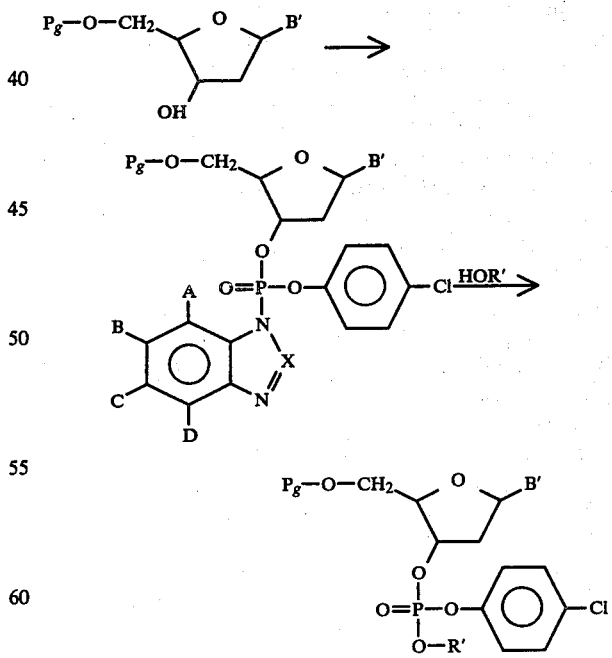

When HOR is a 5' or 3' protected nucleotide either in solution or attached to a solid support, an internucleotide bond is generated without recourse to an external coupling reagent. When R' is a simple lower alkyl of 10 to 6 carbons or such an alkyl substituted with known activating groups like C≡N, SCH₃, CF₃, or the like, so as to give HOR' as a simple alcohol, such as hydroxypropionitrile HO—CH₂—CH₂—CN, a fully protected derivative is produced which has many applications for the production of protected oligonucleotide blocks for synthesis of higher oligomers.

The materials of this invention and their use in oligonucleotide synthesis techniques are further illustrated by the following Examples. These are presented to illustrate the invention and are not intended to limit the invention's scope.

EXAMPLE I

Preparation of Phosphate Triester Coupling Agents

Triisopropylbenzenesulfonyl chloride (15.1 g, 50 mmoles) and 1,2,3-benzotriazole (5.95 g, 50 mmoles) were stirred in dioxan (100 ml). A solution of triethylamine (7 ml, 50 mmoles) in dioxan (20 ml) was added slowly over 10 minutes forming a white precipitate. After 1 hour the solvent was evaporated in vacuo and the residue partitioned between ethyl acetate and water. The organic layer was washed with water (2×), dried over anhydrous magnesium sulphate and evaporated in vacuo to give an oily residue which cyrstallized from petroleum ether to give 18 g (86%) of white needles, determined to be homogeneous by thin layer chromatography (Rf=0.85 on Merck GF 254 plates developed in diisopropyl ether). This white crystalline product was analyzed and determined to be 2,4,6-triisopropylbenzenesulfonyl benzotriazole.

EXAMPLE II

Reaction of mesitylenesulfonyl chloride (10.9 g, 50 mmoles) with 1,2,3-benzotriazole (5.95 g, 50 mmoles) according to the procedure outlined in Example 1 gave 12 g (80%) of crystalline product (Rf=0.75 in TLC conditions described in Example I) analogous to the product of Example I.

EXAMPLE III

The preparation of Example I is repeated substituting an equimolar amount of 4-ethylbenzylsulfonyl chloride for 2,4,6-triisopropylbenzylsulfonyl chloride. The monoethyl analog product is achieved.

EXAMPLES IV-VI

The preparations of Examples I-III are each repeated employing an equimolar amount of 4-chlorobenzotriazole in place of 1,2,3-benzotriazole. In each case, the 4-chlorobenzotriazole analogs are achieved.

EXAMPLES VII-IX

The preparations of Examples I-III are each repeated employing an equimolar amount of benzimidazole in place of the benzotriazole. Benzimidazole analog products are recovered.

EXAMPLE X

Nucleotide Coupling

5'-DMT-N(Bz)-deoxycytidine-3'-p-chlorophenyl phosphate (16 g, 20 mmoles) and N(Bz)-deoxycytidine-3'-p-chlorophenyl-cyanoethyl phosphate (11.5 g, 20 mmoles) were twice co-evaporated to dryness in vacuo from pyridine (100 ml). The residue, in pyridine (50 ml), was treated with triisopropylbenzylsulfonylbenzotriazole (19.2 g, 60 mmoles) as from Example I and N-methylimidazole (4.8 g, 60 mmoles). The mixture was stirred for 4 hours at room temperature, then evaporated in vacuo. The residue was partitioned between ethyl acetate and saturated sodium bicarbonate solution. The organic layer was washed with water (4x), dried over magnesium sulfate and evaporated. The gummy residue was dissolved in chloroform and purified by chromatography on silica gel (Merck 60) eluted with a gradient from 0 to 10% methanol in chloroform (all eluants containing 0.5% pyridine). TLC monitoring of the effluent was employed and appropriate fractions from the column (eluting with 4-5% methanol) were pooled and evaporated. The residue was dissolved in 1:1 chloroform/ethylacetate and passed through a short Sephadex LH-20 gel exclusion column. The eluent was evaporated, dissolved in dioxan and lyophilized to give the dinucleotide as a white powder (18 g, 67% yield).

EXAMPLE XI

Preparation of 5' Dimethoxytrityl-Thymidine-3'-p-chlorophenyl, Cyanoethyl Phosphate Benzotriazole (3.6, 30 mmol) was dissolved in pyridine (15 ml) and treated with p-chlorophenylphosphorodichloridate (1.22, 5 mmol). After 15 minutes, DMT-T (1.6 g, 3 mmol) was added and the reaction mixture left to stand for 30 minutes. 3-hydroxypropionitrile (2.13 g) was added and allowed to react for 1 hour. Water (5 ml) was added and the solvents evaporated in vacuo. The residue was partitioned between ethyl acetate and 1M sodium bicarbonate solution. The organic phase was washed with water (2x) and staturated brine (1x), dried over anhydrous magnesium sulphate, and evaporated. The crude product was purified by silica gel column chromatography eluted with chloroform at a stepwise gradient from 1 to 10 percent methanol (all solvents continuing 0.5% pyridine). The eluant was monitored by thin layer chromatography (product Rf 0.45 CHCl₃/MeOH 10:1); appropriate fractions were pooled and evaporated. The residue was dissolved in 1:1 chloroform/ethylacetate and passed through a short Sephadex LH-20 gel exclusion column. The eluent was evaporated, dissolved in dioxan and lyophilized to give the desired product (2 g, 84%) as a white powder identical to material produced by other synthetic methods.

EXAMPLE XII

Preparation of AT Dimer Using Benzotriazole and p-chlorophenylphosphorodichloridate 5'DMT, N-benzoyldeoxyadenine (1.3 g, 2 mmol) was added to a solution prepared 15 minutes previously of p-chlorophenylhosphorodichloridate (0.48 g, 2 mmol) and benzotriazole (1.19, 10 mmol) in pyridine (5 ml). After 45 minutes, thymidine 3' p-chlorophenyl cyanoethyl phosphate (0.92 g, 1.9 mmol) was added and the mixture left for 2 hours. Water (2 ml) was added and the mixture evaporated and the residue extracted and chromatographed as described in Example XI to give the desired dimer equivalent to alternatively prepared product as a white powder amounting to 1.8 g (70%).

We claim:

1. A benzazolide of the formula

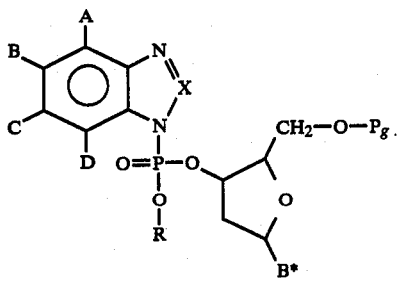

wherein X is N or CH, A, B, C, and D are independently selected from aong hydrogen, chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulfonato amino and cyano, R is a hydrogen or a base labile phosphate protecting group, $P_g$ is a selectively removable protecting group selected from levulinyl and acid labile protecting groups and B* is a base selected from 1-thyminyl, 1-(N-protected)-cytosinyl, 9-(N-protected)adeninyl and 9-(N-protected)quaninyl.

2. The benzazolide of claim 1 characterized as a benzotriazolide wherein X is N.

3. The benzotriazolide of claim 2 wherein B, C and D are hydrogens.

4. The benzotriazolide of claim 3 wherein R is a base-labile phosphate protecting group.

5. The benzotriazolide of claim 4 wherein R is selected from among 1 to 4 carbon alkyls, 6 to 12 carbon aryls, alkaryls and aralkyls and halo-substituted 6 to 12 carbon aryls, alkaryls and aralkyls.

6. The benzotriazolide of claim 5 wherein the N-protected base is protected with a group selected from among benzoyl, isobutryl and anisoyl.

7. A benzazolide of the formula

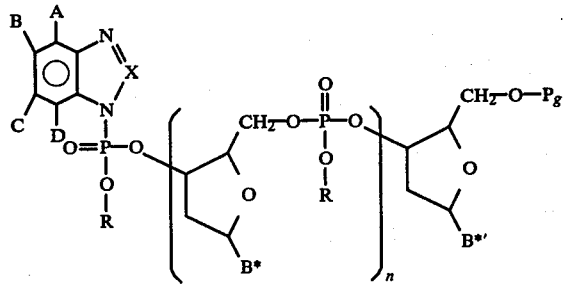

wherein X is N or CH, A, B, C, and D are independently selected from among hydrogen, chloro, bromo, iodo, fluoro, lower alkyls of 1 to 4 carbon atoms, substituted lower akyls, benzyl, phenyl, substituted benzyl, substituted phenyl, lower alkoxies of 1 to 4 carbon atoms, nitro, nitroso, sulfonato amino and cyano, R is a base labile phosphate protecting group, $P_g$ is a selectively removable protecting group selected from levulinyl and acid labile protecting groups and B* and B*' are independently selected from 1-thyminyl, 1-(N-protected)cytosinyl, 9-(N-protected)adeninyl and 9-(N-protected)guaninyl and n is an integer 1 or greater.

8. In a phosphate triester process for coupling deoxynucleotides wherein a first nucleotide having a protected 3' phosphate diester group is reacted under coupling conditions with a second nucleoside or nucleotide having an available free 5' hydroxyl group in the presence of a coupling agent, the improvement comprising employing as said coupling agent an arylsulfonylbenzazolide of the formula

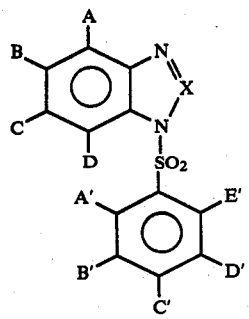

wherein X is CH or N and A, B, C, D, and A', B', C', D' and E' are independently selected from among hydrogen, chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulfonato, amino and cyano.

9. The process of claim 8 wherein B, C and D are hydrogens, B' and D' are hydrogens and A', C' and E' are hydrogens or the same alkyl of 1 to 4 carbon atoms.

10. The process of claim 9 wherein X is N.

11. The process of claim 10 being further characterized as a flow process in which controlled amounts of solutions of said first nucleotide, said second nucleotide or nucleoside and said coupling agent are serially fed for controlled periods into a reaction zone for a reaction period.

12. A process for synthesizing an oligonucleotide comprising a. reacting a nucleotide or nucleoside with a phosphorodibenzazolide of the formula

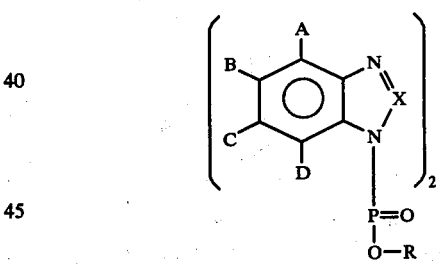

wherein X is N or CH; A, B, C and D are independently selected from hydrogen, chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulfonato amino and cyano, and R is a base-labile phosphate protecting group to yield a phosphorylated nucleotide, and b. coupling said phosphorylated nucleotide with a second nucleotide or nucleoside.

13. A process of claim 12 wherein X is CH.

14. A process of claim 12 wherein X is N.

15. A process for preparing a blocked nucleotide triester which comprises a. reacting a nucleotide or nucleoside with a benzotriazolide of claim 6 to yield a phosphorylated nucleotide, and b. reacting said phosphorylated nucleotide with a blocking alcohol to give a blocked nucleotide triester.

* * * * *